United States Patent [19]

Umemura et al.

[11] 4,072,722

[45] Feb. 7, 1978

[54] PROCESS FOR PREPARING DIHYDRIC PHENOL DERIVATIVES

[75] Inventors: Sumio Umemura; Nagaaki Takamitsu; Toshikazu Hamamoto; Nobuyuki Kuroda, all of Ube, Japan

[73] Assignee: UBE Industries, Ltd., Ube, Japan

[21] Appl. No.: 745,556

[22] Filed: Nov. 29, 1976

Related U.S. Application Data

[63] Continuation of Ser. No. 558,699, March 17, 1975, abandoned.

[30] Foreign Application Priority Data

Apr. 4, 1974 Japan .................................. 49-37319
May 7, 1974 Japan .................................. 49-49812

[51] Int. Cl.² ............................................ C07C 39/08

[52] U.S. Cl. .................................. 260/621 G; 260/625
[58] Field of Search ................ 260/621 G, 610 B, 625

[56] References Cited

U.S. PATENT DOCUMENTS 3,003,000 10/1961 Milas ................................. 260/610 B
3,481,989 12/1969 Vesely et al. .................... 260/621 G Primary Examiner—James O. Thomas, Jr.
Assistant Examiner—Werren B. Lone
Attorney, Agent, or Firm—Flynn & Frishauf

[57] ABSTRACT

A process for preparing dihydric phenol derivatives by oxidizing monohydric phenol derivatives with a ketone peroxide in the presence or absence of sulfuric acid or a salt thereof or a sulfonic acid or a salt thereof.

11 Claims, No Drawings

PROCESS FOR PREPARING DIHYDRIC PHENOL DERIVATIVES

This is a continuation of application Ser. No. 558,699, filed Mar. 17, 1975 now abandoned.

This invention relates to a process for preparing dihydric phenol derivatives. More particularly, it is concerned with a process for preparing dihydric phenol derivatives having the formula (I):

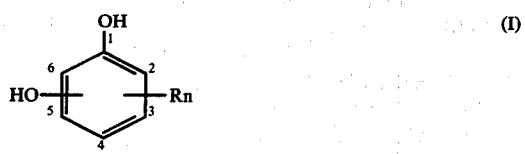

wherein R represents a lower alkyl radical having 1-6 carbon atoms and each R may be the same or different, and n represents zero or an integer of 1 to 4 and when n is 3 or 4, there is no case where all of 2-, 4-, and 6-positions are occupied with the said alkyl radicals which comprises oxidizing monohydric phenol derivatives (II):

wherein R and n have the same meanings as above with a ketone peroxide.

In regard to the preparation of catechol and hydroquinone through oxidation of phenol, many processes have been proposed. For instance, oxidation of phenol with hydrogen peroxide in the presence of ferrous sulfate, copper sulfate etc. has been known for long. [Journal für Partische Chemie N. F., Vol 159, P 45 (1939), von A. Chawala and M. Pailer]. And, there have recently been reported a process wherein phenol is oxidized in the presence of a metal ion such as bismuth, molybdenum, vanadium, titanium etc. (British Pat. No. 1,332,420), a process wherein phenol is oxidized with hydrogen peroxide and an organic peracid in the presence of a strongly acidic sulfonic acid type ion exchange resin (Japanese Patent Provisional Publication No. 36130/1973), a process wherein phenol is oxidized with hydrogen peroxide in the presence of trifluoroacetic acid, an acid of pH 0.7-3 and an organic carboxylic acid (Belgian Pat. No. 786,368) and so forth. These processes, however, give poor yields of dihydric phenols based upon the hydrogen peroxide or organic peracid employed.

As to the previously known principal process wherein a monohydric alkylphenol is oxidized to produce dihydric alkylphenols, there may be mentioned that disclosed in West Germany Patent Application Provisional Publication No. 2,064,497 Specification (Offenlegungsschrift). In this Specification there is disclosed a process wherein various phenols or their derivatives are reacted with hydrogen peroxide in the presence of a strong acid and, in some cases, in an inert organic solvent such as 1,2-dimethoxyethane, chloroform, ethylene dichloride etc. In the Specification is disclosed, with respect to the reaction of a monohydric alkylphenol, an example wherein p-cresol is oxidized with perchloric acid, phosphoric acid and hydrogen peroxide without any particular addition of an organic solvent to give 1,2-dihydroxy-4-methylbenzene. The yield in this example, however, is considered to be unsatisfactory.

We have conducted research into a process for preparing the desired compounds, namely dihydric phenol derivatives having the formula (I), which is a technically simple procedure, in a remarkably high yield of dihydric phenol derivatives based upon the ketone peroxide employed and commercially inexpensive and thus we have completed the present invention.

It is, accordingly, an object of this invention to provide a process for preparing dihydric phenol derivatives having the formula (I) in a high yield based upon the ketone peroxide employed.

Another object of this invention is to provide a process for preparing the desired compounds at a low cost.

Still another object of this invention is to provide a reaction process wherein the desired compounds can be readily separated from the reaction mixture.

Other objects of this invention are apparent from the following explanation and examples.

This invention is concerned with a process for preparing dihydric phenol derivatives wherein monyhydric phenol derivatives are oxidized with a ketone peroxide. According to the present process, dihydric phenol derivatives can be produced in a higher yield than that in the prior process and a step for the separation of the so produced dihydric phenol derivatives from the reactant can be readily accomplished since an oxidizing agent, ketone peroxide is converted to water and ketone after completion of the reaction. Moreover, the present process is economical, since a high yield is obtained with respect to a ratio to the ketone peroxide employed.

When n represents zero, it is clear that the formula (II) contains phenol.

R, which is used in formulas (I) and (II), represents a straight or branched alkyl radical having 1-6 carbon atoms. As the alkyl group may be mentioned, for example, methyl, ethyl, propyl, isopropyl, butyl, sec-butyl, tert-butyl, isobutyl, pentyl, hexyl etc. As the monohydric alkylphenols having such alkyl group may be mentioned, for example, o-, m- or p-cresol, o-, m- or p-ethylphenol, o-propylphenol, p-isopropylphenol, m-butylphenol, p-sec-butylphenol, p-tert-butylphenol, m-isobutylphenol, p-pentylphenol, p-hexylphenol, 2,3-dimethylphenol, 2,5-dimethylphenol, 3,4-dimethylphenol, 2,4-dimethylphenol, 2,6-dimethylphenol, 3,5-dimethylphenol, 2,3,4-trimethylphenol, 2,3,6-trimethylphenol, 2,4,5-trimethylphenol, 2,3,5-trimethylphenol, 3,4,5-trimethylphenol, 2,3,4,5-tetramethylphenol, 2,3,5,6-tetramethylphenol, 2-ethyl-3-methylphenol, 3-tert-butyl-4-methylphenol, 2-isopropyl-5-methylphenol, 2-pentyl-6-methylphenol, 3-hexyl-5-methylphenol and the like.

This invention will be explained in detail hereinbelow.

As the ketone peroxides which may be employed in this invention are satisfactorily usable even commercially available ones and these peroxides are synthesized by a conventional reaction of a ketone with hydrogen peroxide or autoxidation of secondary alcohols and have at least one or more of the structures as defined below in their molecules.

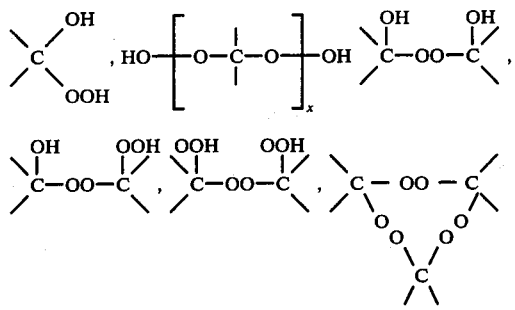

wherein x represents an integer of 1-4.

In the above-mentioned structures two bonds may be combined together to form a 5-6 membered ring.

As the ketone which may be employed for the production of the ketone peroxide may be mentioned any types of ketones and, for example, the following ketones are given.

1. a ketone having 3-20 carbon atoms and represented by the following general formula (III):

wherein $R_1$ and $R_2$ may be the same or different and each represents a straight or branched alkyl group of 1-18 carbon atoms or phenyl group, the hydrogen of said alkyl groups being optionally substituted with a halogen atom, hydroxy group, amino group or phenyl group, and $R_1$ and/or $R_2$ may be an aliphatic group having an unsaturation bond;

2. a diketone having 3-20 carbon atoms and represented by the following general formula (IV):

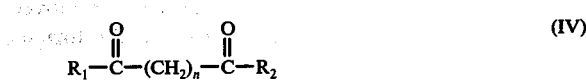

wherein n is an integer of 0-16 inclusive and $R_1$ and $R_2$ have the same meanings as above;

3. a cycloketone having the following general formula (V):

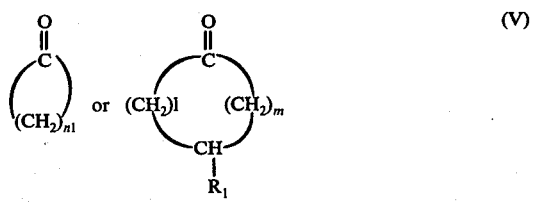

wherein $n_1$ represents an integer of 4-11 inclusive, $l + m$ represents an integer of 3-10 inclusive and $R_1$ has the same meaning as above.

In the aliphatic ketone having the above-mentioned general formula (III), examples of the straight or branched alkyl groups of 1-18 carbon atoms in $R_1$ and $R_2$ are as follows: Methyl, ethyl, propyl, 1-methylethyl, butyl, 1-methylpropyl, 1,1-dimethyl-ethyl, 2-methylpropyl, pentyl, 1-methylbutyl, 2-methylbutyl, 3-methylbutyl, 1,2-dimethylpropyl, hexyl, 1-methylpentyl, octyl, decyl, undecyl, 2-dodecyl, tridecyl, tetradecyl, pentadecyl, octadecyl etc.

Representative examples of the ketones having the above-mentioned alkyl groups are as follows:

Acetone, methylethylketone, 2-pentanone, 3-pentanone, 3-methyl-2-butanone, 2-hexanone, 3-hexanone, 3-methyl-2-pentanone, 4-methyl-2-pentanone, 3,3-dimethyl-2-butanone, 2-heptanone, 3-heptanone, 4-heptanone, 2,4-dimethyl-3-pentanone, 2-octanone, 6-methyl-2-heptanone, 2-nonanone, 2,6-dimethyl-4-heptanone, 2,2,4,4-tetramethyl-3-heptanone, 3-decanone, 6-undecanone, 2-tridecanone, 7-tridecanone, 2-tetradecanone, 2-pentadecanone, 2-hexadecanone, 2-heptadecanone, 3-octadecanone, 4-nonadecanone, 5-eicosanone, etc.

The unsaturation bond which the aliphatic ketones having the above-mentioned general formula (III) involve may be any of double and triple bonds, but double bond is preferable.

As the ketones having an unsaturation bond may be mentioned the following:

3-Buten-2-one, 3-penten-2-one, 5-hexen-2-one, 4-methyl-3-penten-2-one, 6-methyl-5-hepten-2-one, 5-octen-2-one, 7-nonadecen-2-one, etc.

Examples of the ketones having the above-mentioned general formula (III) which have a phenyl group or the alkyl groups substituted with a halogen atom particularly a chlorine atom, bromine atom and hydroxy group, amino group and phenyl group are as follows:

1-chloro-2-propanone, 1-chloro-3-heptanone, 3-hydroxy-2-butanone, 1-bromo-3-heptanone, 1-hydroxy-2-propanone, 4-amino-4-methyl-2-pentanone, methylphenylketone, benzophenone, 1-phenyl-2-propanone, 1-phenyl-1-butanone, 1-phenyl-3-butanone, 1-phenyl-3-pentanone, 1,3-diphenyl-2-propanone, etc.

Examples of the diketones having the general formula (IV) are as follows:

2,3-Butanedione, 2,4-pentanedione, 2,5-hexanedione, etc.

Examples of the cycloketones having the general formula (V) are as follows:

Cyclopentanone, cyclohexanone, 2-ethyl-1-cyclopentanone, 2-methyl-1-cyclohexanone, cyclododecanone, etc.

And, the ketone peroxide can be easily produced through autoxidation of a secondary alcohol in a well-known manner.

As the secondary alcohol which may be employed in this invention may be any types of secondary alcohols and, for example, may be mentioned the following.

1. A secondary alcohol having 3-20 carbon atoms and represented by the following general formula (VI):

wherein $R_1$ and $R_2$ have the same meanings as above;

2. a di-secondary alcohol having 3-20 carbon atoms and represented by the following general formula (VII):

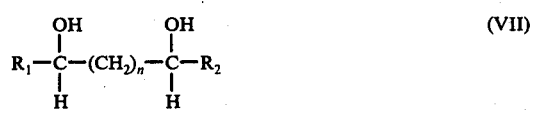

wherein $R_1$, $R_2$ and n have the same meanings as above;

3. a cycloalcohol having the following general formula (VIII)

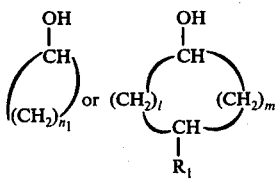

(VIII)

wherein $R_1$, $n_1$, $l$ and $m$ have the same meanings as above.

These secondary alcohols (VI), (VII) and (VIII) correspond to the ketones (III), (IV) and (V), respectively. Representative examples of such alcohols are given below.

As examples of those aliphatic secondary alcohols represented by the above-mentioned general formula (VI) wherein $R_1$ and $R_2$ are straight or branched alkyl groups of 1-18 carbon atoms may be mentioned the following:

2-propanol, 2-butanol, 2-pentanol, 3-pentanol, 3-methyl-2-butanol, 2-hexanol, 3-hexanol, 3-methyl-2-pentanol, 4-methyl-2-pentanol, 3,3-dimethyl-2-butanol, 2-heptanol, 3-heptanol, 4-heptanol, 2,4-dimethyl-3-pentanol, 2-octanol, 6-methyl-2-heptanol, 2-nonanol, 2,6-dimethyl-4-heptanol, 2,2,4,4-tetramethyl-3-pentanol, 3-decanol, 6-undecanol, 2-tridecanol, 7-tridecanol, 2-tetradecanol, 2-pentadecanol, 2-hexadecanol, 2-heptadecanol, 2-octadecanol, 3-octadecanol, 4-nonadecanol, 5-eicosanol, etc.

Unsaturation bond in the aliphatic secondary alcohol having the above-mentioned general formula (VI) may be a double or a triple bond, but a double bond is preferable. As the secondary alcohols having an unsaturation bond may be mentioned the following:

3-Buten-2-ol, 3-penten-2-ol, 5-hexen-2-ol, 4-methyl-3-penten-2-ol, 6-methyl-5-hepten-2-ol, 5-octen-2-ol, 7nonadecen-2-ol, etc.

As examples of the secondary alcohols having the above-general formula (VI) wherein $R_1$ and $R_2$ are a phenyl group or alkyl groups substituted with a halogen atom, particularly a chlorine atom and bromine atom, hydroxy group, amino group and phenyl group may be mentioned the following:

1-chloro-2-butanol, 1-chloro-3-heptanol, 3-hydroxy-2-butanol, 1-bromo-3-heptanol, 1-hydroxy-2-propanol, 4-amino-4-methyl-2-pentanol, 1-phenylethanol, diphenylmethanol, 1-phenyl-2-propanol, 1-phenyl-1-butanol, 1-phenyl-3-butanol, 1-phenyl-3-pentanol, 1,3-diphenyl-2-propanol, etc.

As examples of the secondary dihydric alcohols having the above-mentioned general formula (VII) may be mentioned the following:

2,3-Butanediol, 2,4-pentanediol, 2,5-hexanediol, etc.

As examples of the secondary alcohols having the above-mentioned general formula (VIII) may be mentioned the following:

Cyclopentanol, cyclohexanol, 2-ethyl-1-cyclopentanol, 2-methyl-1-cyclohexanol, etc.

Particularly preferable ketones and alcohols which may be employed in this invention are the $C_3$-$C_{15}$ saturated aliphatic monoketones and monoalcohols, the $C_5$-$C_{12}$ saturated alicyclic monoketones and monoalcohols and the aromatic monoketones and monoalcohols, all of which have no substituents.

In the present invention, oxidation of monohydric phenol derivatives with the ketone peroxide as stated above is effected under the following conditions.

An amount of the ketone peroxide employed is not particularly critical, but the peroxide amount P per m.mole of monohydric phenol derivatives is a value of from 0.005 to 1.00, preferably 0.01-0.50. The above-mentioned peroxide amount "P" is expressed by the following equation:

$$P = \frac{a \times b \times 10}{16}$$

a: active oxygen amount (%)
b: ketone peroxide weight (g)

The term "active oxygen" as used herein is meant to indicate one oxygen atom in the oxygens constituting a peroxide bond-O.O-and said oxygen atom is capable of effecting the following reactions when the corresponding peroxide is added to hydrochloric acid-potassium iodide or acetic acid-potassium iodide:

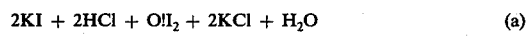 (a)

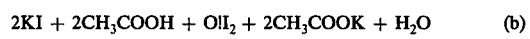 (b)

The term "active oxygen amount" as used herein is meant to be a weight percentage of the active oxygen contained in a sample peroxide and its determination is done by making a peroxide participate in the above reaction (a) or (b) and measuring the so liberated iodine.

The reaction is conducted at a temperature of 0°-250° C., preferably 45°-200° C. A solvent may not be used, but, if used there may be used those solvents that do not prevent the oxidation reaction, such as methyl acetate, ethyl acetate, ethylene diacetate, methyl benzoate, dimethyl phthalate, diethyl phthalate, benzene, etc. as well as various ketones such as acetone, methyl ethyl ketone, 2-pentanone, 3-pentanone, 3-methyl-2-butanone, 2-hexanone, 3-hexanone, 4-methyl-2-pentanone, 3,3-dimethyl-2-butanone, cyclopentanone, methyl phenyl ketone, etc. The reaction period may vary upon the reaction temperature and the presence and amount of a catalyst as set forth below. The reaction period is not particularly critical. The reaction may be effected at atmospheric pressure, but it may be effected at a reduced pressure or under pressure. For improved yield of dihydric phenol derivatives, a water content in the reaction system should be desirably as low as possible.

The present reaction may be effected without any use of a catalyst, but the reaction is preferably conducted in the presence of the catalyst as stated below. The catalyst which may be employed in the present reaction is sulfuric acid, preferably conc. sulfuric acid, or its salts or sulfonic acids or its salts. As the salts of sulfuric acid may be employed various metal salts and organic base salts and there is no limitation upon the sorts of metals and organic bases. As the type of the salt may be any type of a normal salt, an acidic salt, a double salt and a complex salt. Namely, there may be used any salts if they contain sulfate ion. The sulfate, if having water of crystallization, may be utilized as such. Examples of the sulfates are as follows:

Ammonium sulfate, lithium bisulfate, sodium sulfate, sodium bisulfate, magnesium sulfate, aluminum sulfate, potassium bisulfate, copper sulfate, zinc sulfate, titanium sulfate, chromium sulfate, manganese sulfate, iron sulfate, ammonium ferrous sulfate, cobalt sulfate, nickel sulfate, potassium aluminum sulfate, silver sulfate, cadmium sulfate, indium sulfate, zirconium sulfate, tin sulfate, antimony sulfate, molybdenum sulfate, ruthenium sulfate, barium sulfate, mercury sulfate, thallium sulfate, lead sulfate, cerium sulfate, hydroxylamine sulfate, dibutylamine sulfate, aniline sulfate, pyridine sulfate, piperidine sulfate, etc.

As sulfonic acids may be employed aliphatic sulfonic acids such as methanesulfonic acid, ethanesulfonic acid and the like, aromatic sulfonic acids such as benzenesulfonic acid, p-toluenesulfonic acid, p-phenolsulfonic acid, p-aminosulfonic acid, naphthalene-α-sulfonic acid and the like as well as sulfonic acid type resins such as strongly acidic ion exchange resins. As the salts of sulfonic acids may be employed various salts such as metal salts, organic base salts, etc. similarly to the above sulfates. A catalyst may be used as a homogeneous or heterogeneous system.

In the case of the heterogeneous system, the catalyst may be applied in various forms such as a suspended state or tablet form. An amount of the catalyst may vary in a wide range, but it is desirable for a satisfactory reaction rate to employ the catalyst not less than 0.0001% by weight with respect to a monohydric phenol derivative.

In the foregoing a batchwise practice of the present reaction was illustrated, but it is to be noted that a continuous reaction of the present invention may be also practised. More specifically, there may be mentioned a process wherein a stock flow is continuously supplied to a catalyst layer for reaction, a process wherein a catalyst is suspended or dissolved in a stock flow and the resultant is passed through a reaction zone and so forth. In the latter case, the required amount of a catalyst may be determined according to the batchwise system.

For separation of the desired product after completion of the reaction, well-known procedures may be applied, as the present reaction does not involve any matters to prevent the desired product from separation, and, for example, the desired product may be easily separated by cooling the reaction mixture and subjecting it to fractional distillation, in many cases after removal of the catalyst. Namely, water, the ketone, the monohydric phenol derivatives and the dihydric phenol derivatives thus produced are separated by fractional distillation. The so separated ketone and monohydric phenol derivatives are recycled for reuse in the next reaction.

The dihydric phenol derivatives thus obtained may be obtained either as a substantially single compound or in the form of a mixture of several types, depending upon the structure of a starting monohydric phenol derivatives (II). For instance, where phenol is employed as a starting material, a mixture of catechol and hydroquinone is formed. Where an o-alkylphenol is employed as a starting material, a mixture of a 3-alkylcatechol and a 2-alkylhydroquinone is obtained. Where an m-alkylphenol is employed as a starting material, a mixture of a 3-alkylcatechol, a 4-alkylcatechol and a 2-alkylhydroquinone is obtained. Where a p-alkylphenol is employed as a starting material, a 4-alkylcatechol mainly is obtained. Where a mixture of two or more of the monohydric alkylphenols is employed as a starting material, dihydric alkylphenols are obtained in the form of a mixture thereof according to the above-depicted principle.

When monohydric polyalkylphenol derivatives are employed as starting materials, the products are tabulated in Table 1 as follows.

Table 1

| Monohydric polyalkylphenol derivatives as starting material | Products |
| --- | --- |
| 2,3-dimethylphenol | 3,4-dimethylcatechol, 2,3-dimethylhydroquinone |
| 2,4-dimethylphenol | 3,5-dimethylcatechol |
| 2,5-dimethylphenol | 3,6-dimethylcatechol, 2,5-dimethylhydroquinone |
| 2,6-dimethylphenol | 2,6-dimethylhydroquinone |
| 3,4-dimethylphenol | 3,4-dimethylcatechol, 4,5-dimethylcatechol |
| 3,5-dimethylphenol | 3,5-dimethylcatechol, 2,6-dimethylhydroquinone |
| 2-isopropyl-5-methylphenol | 3-isopropyl-6-methyl-catechol, 2-isopropyl-5-methyl-hydroquinone |
| 2,3,4-trimethylphenol | 3,4,5-trimethylcatechol |
| 2,3,5-trimethylphenol | 3,4,6-trimethylcatechol, 2,3,5-trimethylhydroquinone |
| 2,3,6-trimethylphenol | 2,3,6-trimethylhydroquinone |
| 3,4,5-trimethylphenol | 3,4,5-trimethylcatechol |
| 2,4,5-trimethylphenol | 3,4,6-trimethylcatechol |
| 2,3,5,6-tetramethylphenol | 2,3,5,6-tetramethylhydroquinone |
| 2,3,4,5-tetramethylphenol | 3,4,5,6-tetramethylcatechol |

The dihydric phenol derivatives thus obtained may be employed as intermediates for the production of a dyestuff, an anti-oxidant or a drug in the form of a single compound or, where it is obtained as a mixture, the mixture can be used as such or after separation as required.

The process of this invention is more concretely illustrated by the following examples, but these examples are not limiting the process of this invention.

The ketone peroxide which is employed in the following examples 1–36 is the same as defined below or produced in the same manner as shown below.

METHOD FOR THE SYNTHESIS OF A KETONE PEROXIDE

1. Methyl ethyl ketone peroxide (manufactured by Nihon Yushi K.K., Permec N)
   a 55% by weight solution of methyl ethyl ketone peroxide dissolved in dimethyl phthalate. Active oxygen amount 16.4%.
2. 4-methyl-2-pentanone peroxide (synthesized)
   To a stirred mixture of 45 g. (0.397 mole) of 30% hydrogen peroxide solution and 28.8 g of 100% $H_3PO_4$ is added 27.7 g. (0.277 mole) of 4-methyl-2-pentanone at 20°–25° C. and, after stirring for about 10 minutes, the mixture is allowed to stand. A peroxide layer is separated, neutralized with calcium carbonate and filtered. Active oxygen amount 7.09%.
3. Cyclopentanone peroxide (synthesized)
   This peroxide is synthesized in the same manner as in the above 2) except that 23.3 g. (0.277 mole) of cyclopentanone is employed instead of the 4-methyl-2-pentanone. Active oxygen amount 14.3%.
4. Methylphenyl ketone peroxide (synthesized)
   This peroxide is synthesized in the same manner as in the above 2) except that 33.2 g. (0.277 mole) of methyl phenyl ketone is employed instead of the 4-methyl-2-pentanone. Active oxygen amount 3.73%.

EXAMPLES 1–4

In a 50 ml-volume flask with a flat bottom, which was equipped with a reflux condenser, a thermometer, a stirrer and an outlet for liquid, the ketone peroxide indicated in Table 2 was added to 10 g. (106 m.moles) of phenol so that a peroxide amount P may be 5.30 and the reaction was effected with stirring in an oil bath at 170° C. for 120 minutes. The reaction mixture was analyzed by a gas chromatography and yields of catechol and hydroquinone on peroxide basis as defined hereinbelow are shown in Table 2.

$$\text{yield of catechol}(\%) = \frac{\text{m.mole number of the catechol produced}}{\text{peroxide amount (P) charged}} \times 100$$

$$\text{yield of hydroquinone}(\%) = \frac{\text{m.mole number of the hydroquinone produced}}{\text{peroxide amount (P) charged}} \times 100$$

Yields of catechol and hydroquinone are shown in Table 2.

Table 2

| Example | Peroxide Sort | Amount to be added (g) | CT yield (%) | HQ yield (%) | (CT+HQ) yield (%) | CT/HQ (molar ratio) |
|---|---|---|---|---|---|---|
| 1 | methyl ethyl ketone peroxide | 0.94 | 30.1 | 20.2 | 50.3 | 1.49 |
| 2 | 4-methyl-2-pentanone peroxide | 1.20 | 34.4 | 17.5 | 51.9 | 1.97 |
| 3 | cyclopentanone peroxide | 0.59 | 32.3 | 19.3 | 51.6 | 1.67 |
| 4 | methyl phenyl ketone peroxide | 2.27 | 29.6 | 22.2 | 51.8 | 1.33 |
| Comparative 1 | 60% hydrogen peroxide | 0.30 | 26.6 | 13.2 | 39.8 | 2.02 |

In the table CT represents catechol and HQ represents hydroquinone.

EXAMPLES 5-8

With 10 g. (106 m.moles) of phenol was admixed the ketone peroxide as listed in Table 3 so that a peroxide amount (P) may be 5.30. To the mixture was added 0.70 g. of indium sulfate (In$_2$(SO$_4$)$_3$.9H$_2$O) and then the reaction was carried out at 100° C. for 30 minutes. Yields of catechol and hydroquinone are shown in Table 3.

Table 3

| Example | Peroxide Sort | Amount to be added (g) | CT yield (%) | HQ yield (%) | (CT+HQ) yield (%) | CT/HQ (molar ratio) |
|---|---|---|---|---|---|---|
| 5 | methyl ethyl ketone peroxide | 0.94 | 55.5 | 40.6 | 96.1 | 1.37 |
| 6 | 4-methyl-2-pentanone peroxide | 1.20 | 54.7 | 36.1 | 90.8 | 1.52 |
| 7 | cyclopentanone peroxide | 0.59 | 50.3 | 32.5 | 82.8 | 1.55 |
| 8 | methyl phenyl ketone peroxide | 2.27 | 52.5 | 34.0 | 86.5 | 1.54 |

COMPARATIVE EXAMPLE 1

The reaction was effected in the same manner as in Example 1 except that 0.30 g (5.30 m. moles) of 60% hydrogen peroxide was added instead of the ketone peroxide.

EXAMPLES 9-27

A mixture of 10 g. (106 m.moles) of phenol, 0.857 g. (peroxide amount p = 4.83) of methyl ethyl ketone peroxide and the catalyst shown in Table 4 was reacted at 100° C. for 30 minutes in the same manner as in Example 1. Yields of catechol and hydroquinone are shown in Table 4.

Table 4

| Example | Catalyst Sort | Amount to be added (g) | CT yield (%) | HQ yield (%) | (CT+HQ) yield (%) | CT/HQ (molar ratio) |
|---|---|---|---|---|---|---|
| 9 | H$_2$SO$_4$ (98%) | 0.020 | 46.3 | 34.2 | 80.5 | 1.35 |
| 10 | NaHSO$_4$ . H$_2$O | 0.375 | 58.6 | 40.4 | 99.0 | 1.45 |
| 11 | Al$_2$(SO$_4$)$_3$ . 18H$_2$O | " | 48.9 | 38.5 | 87.4 | 1.27 |
| 12 | AlK(SO$_4$)$_2$ | " | 47.0 | 33.8 | 80.8 | 1.39 |
| 13 | KHSO$_4$ | " | 58.7 | 38.5 | 97.2 | 1.52 |
| 14 | CuSO$_4$ | " | 50.3 | 35.0 | 85.3 | 1.44 |
| 15 | NiSO$_4$ . 6H$_2$O | " | 49.2 | 37.5 | 86.7 | 1.31 |
| 16 | ZnSO$_4$ . 7H$_2$O | " | 57.1 | 34.2 | 91.3 | 1.67 |
| 17 | Ti$_2$(SO$_4$)$_3$ | " | 49.5 | 33.8 | 83.3 | 1.46 |
| 18 | In$_2$(SO$_4$)$_3$ . 9H$_2$O | " | 58.5 | 37.4 | 95.9 | 1.56 |
| 19 | Ce(SO$_4$)$_2$ . 4H$_2$O | " | 53.5 | 32.8 | 86.3 | 1.63 |
| 20 | Fe$_2$(SO$_4$)$_3$ . 9H$_2$O | " | 53.2 | 36.9 | 90.1 | 1.44 |
| 21 | Al$_2$(SO$_4$)$_3$ . (NH$_4$)$_2$SO$_4$ . 24H$_2$O | " | 47.3 | 33.9 | 81.2 | 1.40 |
| 22 | (NH$_2$OH)$_2$ , H$_2$SO$_4$ | " | 55.7 | 34.2 | 89.9 | 1.63 |
| 23 | benzenesulfonic acid | 0.050 | 54.5 | 34.2 | 88.7 | 1.59 |
| 24 | p-phenolsulfonic acid | 0.050 | 52.5 | 34.8 | 87.3 | 1.51 |
| 25 | p-toluenesulfonic acid | 0.050 | 51.6 | 25.1 | 76.7 | 2.06 |
| 26 | strongly acidic ion exchange resin Amberlyst 15 (available from Rohm & Haas Co.) | 0.375 | 58.1 | 40.6 | 98.7 | 1.43 |
| 27 | strongly acidic ion | 0.100 | 52.0 | 35.3 | 87.3 | 1.47 |

Table 4-continued

| Example | Sort | Catalyst Amount to be added (g) | CT yield (%) | HQ yield (%) | (CT+HQ) yield (%) | CT/HQ (molar ratio) |
|---|---|---|---|---|---|---|
| | exchange resin Dowex 50wx4 (available from Dow Chemical Co.) | | | | | |

EXAMPLES 28–32

Proportions of methyl ethyl ketone peroxide and $In_2(SO_4)_3 \cdot 9H_2O$ to 10 g. (106 m.moles) of phenol and reaction temperatures were selected and used as shown in Table 5. The reaction was carried out for 30 minutes in the same manner as in Example 1. Yields of catechol and hydroquinone are shown in Table 5.

Table 5

| Example | Methyl ethyl ketone peroxide amount (P) | Phenol (1 m.mole) | $In_2(SO_4)_3 \cdot 9H_2O$ (g) | Reaction temperature (° C) | CT yield (%) | HQ yield (%) | (CT+HQ) yield (%) | CT/HQ (molar ratio) |
|---|---|---|---|---|---|---|---|---|
| 28 | 0.028 | | 0.375 | 100 | 57.3 | 41.3 | 98.6 | 1.39 |
| 29 | 0.151 | | " | " | 50.8 | 32.9 | 83.7 | 1.54 |
| 30 | 0.042 | | 0.050 | " | 55.5 | 40.6 | 96.1 | 1.37 |
| 31 | " | | 0.375 | 150 | 57.6 | 37.0 | 94.6 | 1.56 |
| 32 | " | | " | 45 | 49.6 | 35.2 | 84.8 | 1.41 |

EXAMPLE 33

Into a 3l-volume flask equipped with a reflux condenser, a thermometer, a stirrer and an outlet for liquid were charged 1950 g. (20.74 moles) of phenol and 234.0 g. (P=1037) of 4-methyl-2-pentanone peroxide and the flask was maintained at 50° C. 13.1 g. of sodium bisulfate ($NaHSO_4 \cdot H_2O$) was added thereto and the flask was dipped in an oil bath at 113° C. so that the reaction could proceed. After 3 minutes and 1 hour from addition of the catalyst, 5 g. portions of the reaction mixture were withdrawn and analyzed by a gas chromatography. After 10 hours, the whole reaction mixture was cooled to 50° C., the catalyst was removed by extraction with water and the residue was subjected to vaccum distillation to separate water, 4-methyl-2-pentanone, phenol, 63.0 g. (0.572 mole) of catechol and 42.8 g. (0.389 mole) of hydroquinone. Changes in yields of catechol and hydroquinone upon time lapse are summarized in Table 6.

Table 6

| Reaction period | CT yield (%) | HQ yield (%) | (CT+HQ) yield (%) | CT/HQ (molar ratio) |
|---|---|---|---|---|
| 3 minutes | 57.9 | 39.2 | 97.1 | 1.48 |
| 1 hour | 58.5 | 39.7 | 98.2 | 1.47 |
| 10 hours | 55.5 | 37.7 | 93.2 | 1.47 |

EXAMPLE 34

Into the same reaction vessel as in Example 33 were charged 2010 g. (21.38 moles) of phenol and 245 g. (P=1086) of 4-methyl-2-pentanone peroxide and the vessel was maintained at 90° C. To the resulting mixture was added 10.1 g. of aluminum sulfate ($Al_2(SO_4)_3 \cdot 18H_2O$) and the flask was dipped in an oil bath at 115° C. for 30 minutes. Thereafter, the reaction mixture was cooled to 50° C. and the catalyst suspending in the reaction mixture was removed by filtration. The filtrate was distilled in the same manner as in Example 33 to recover 60.1 g. (0.546 mole) of catechol and 48.0 g. (0.437 mole) of hydroquinone. A total yield of catechol and hydroquinone was 90.2%.

EXAMPLE 35

50 g. (531 m.moles) of phenol, 5.99 g. (P=26.6) of 4-methyl-2-pentanone peroxide and 0.4 mg. of 98% sulfuric acid were mixed and reacted at 50° C. for 15 minutes in the same manner as in Example 1 and 1.54 g. of catechol and 1,03 g. of hydroquinone were obtained. The total yield of catechol and hydroquinone was 87.5%.

EXAMPLE 36

In a vessel used in Example 33 were placed 1917 g. (20.37 moles) of phenol, 230 g. (P=1019) of 4-methyl-2-pentanone peroxide and 0.10 g. of 98% sulfuric acid and the mixture was stirred at 50° C. in an oil bath for 10 minutes. After adding 0.16 g. of 50% aqueous sodium hydroxide to the reaction mixture and neutralizing sulfuric acid, the reaction mixture was subjected to vacuum distillation to fractionate water, 176 g. of 4-methyl-2-pentanone, 1824 g. (19.38 moles) of phenol, 58.9 g. (0.535 mole) of catechol and 40.4 g. (0.367 mole) of hydroquinone. The yield of catechol and hydroquinone based on peroxide basis is 88.5% and that of based on phenol was 91.1%.

EXAMPLE 37.

a. synthesis of ketone peroxide by autoxidation of secondary alcohol.

In a glass autoclave equipped with a reflux condenser having an inlet and outlet for gas, thermometer, and stirrer was placed 167 g. of sec. butanol and heated in an oil bath. After the temperature of the reaction mixture was reached to 110° C., the pressure in the autoclave was maintained at 5 kg./cm$^2$ and oxygen was bubbled into it at a rate of 18 l/hr. (calculated at 0° C. under atmospheric pressure) and the mixture was reacted for 5 hours. After completion of the reaction, methyl ethyl ketone peroxide produced was analyzed by a iodometry. The amount of active oxygen in the reaction mixture was 2.97%. By using this autoxidation liquid of sec. butanol containing methyl ethyl ketone peroxide, the next examples were carried out.

b. In a vessel used in Example 1 were placed 10.0 g. (106 m.moles) of phenol, 2.17 of autoxidation liquid of sec. butanol which contained methyl ethyl ketone peroxide (P=4.03) and 0.004 g. of 98% sulfuric acid. The reaction mixture was stirred at 100° C. for 30 minutes and the products were analyzed by a gas chromatography. 0.153 g. of (1.39 m.moles) of catechol and 0.073 g. (0.66 m.mole) of hydroquinone were obtained. The total yield of these compounds was 50.8%.

EXAMPLE 38

By following in the same manner as in Example 37(b) except that 0.10 g. of indium sulfate (In$_2$(SO$_4$)$_3$.9H$_2$O) was used instead of sulfuric acid, 0.0150 g. (1.36 m.moles) of catechol and 0.071 g. (0.64 m.moles) of hydroquinone were obtained. The total yield of these compounds was 50.1%.

The ketone peroxide which is employed in the following example 39-54 is the same as defined below or produced in the same manner as shown below.

METHOD FOR THE SYNTHESIS OF A KETONE PEROXIDE

5. Methyl ethyl ketone peroxide (manufactured by Nihon Yushi K.K., Permec N)
    a 55% by weight solution of methyl ethyl ketone peroxide dissolved in dimethyl phthalate. Active oxygen amount 17.5%.
6. 4-Methyl-2-pentanone peroxide (synthesized)
    This peroxide is synthesized in the same manner as in the above 2), and the unreacted ketone is distilled off under reduced pressure to give a sample. Active oxygen amount 16.9%.
7. Cyclopentanone peroxide (synthesized)
    This peroxide is synthesized in the same manner as in the above 3) except that 46.6 g. (0.554 mole) of cyclopentanone is employed. Active oxygen amount 6.51%.
8. Methylphenyl ketone peroxide (synthesized)
    This peroxide is synthesized in the same manner as in the above 4). Active oxygen amount 3.73%.

EXAMPLE 39

Into a 300 ml-volume four necked flask, which was equipped with a reflux condenser, a thermometer, a stirrer and an outlet for liquid, were charged 150 g. (1390.0 m.moles) of m-cresol and 4.38 g. (P=46.3) of 4-methyl-2-pentanone peroxide and this flask was dipped in an oil bath at 120° C. The reaction was carried out with stirring for 90 minutes. The reaction mixture was analyzed by a gas chromatography to give 1.15 g. (9.3 m. moles) of 3-methylcatechol, 1.09 g. (8.8 m.moles) of 4-methyl catechol and 1.38 g. (11.1 m.moles) of 2-methylhydroquinone. Yield of dihydric phenols upon peroxide basis as defined below was 63.1%.

$$\text{Yield of dihydric alkylphenols} = \frac{\text{millimole number of all dihydric alkylphenols produced}}{\text{peroxide amount (P) charged}} \times 100$$

EXAMPLE 40

The reaction was carried out in the same manner as in Example 39 except that 19.86 g. (P=46.3) of methyl phenyl ketone peroxide was charged instead of the 4-methyl-2-pentanone peroxide to give 0.99 g. (8.0 m.moles) of 3-methylcatechol, 1.20 g. (9.7 m.moles) of 4-methylcatechol and 1.15 g. (9.3 m.moles) of 2-methylhydroquinone. Yield of dihydric alkylphenols (upon the peroxide basis; this basis will be frequently referred to herein below), 58.3%.

COMPARATIVE EXAMPLE 2

The reaction was carried out in the same manner as in Example 39 except that 2.56 g. (45.2 m.moles) of 60% hydrogen peroxide solution was charged instead of the 4-methyl-2-pentanone peroxide to give 0.68 g. (5.5 m.moles) of 3-methylcatechol, 0.80 g. (6.4 m.moles) of 4-methylcatechol and 0.94 g. (7.6 m.moles) of 2-methylhydroquinone. The yield of dihydric alkylphenols was 43.1%.

EXAMPLE 41

Into the same reaction vessel as in Example 39 were charged 150 g. (1390 m.moles) of o-cresol, 7.70 g. (P=46.3) of methyl ethyl ketone peroxide and 0.40 g. of sulfuric acid and the flask was dipped in an oil bath at 100° C. The reaction was carried out for 30 minutes in the same manner as in Example 39 to give 2.70 g. (21.8 m.moles) of 3-methylcatechol and 1.54 g. (12.4 m.moles) of 2-methylhydroquinone. The yield of dihydric alkylphenols was 74.1%.

EXAMPLE 42

The reaction was carried out in the same manner as in Example 41 except that 11.54 g. (P=69.4) of methyl ethyl ketone peroxide was employed instead of the 7.70 g. to give 4.16 g. (33.5 m.moles) of 3-methylcatechol and 1.95 g. (15.7 m.moles) of 2-methylhydroquinone. The yield of dihydric alkylphenols was 70.9%.

EXAMPLE 43

The reaction was carried out in the same manner as in Example 42 except that 1.00 g. of sodium bisulfate (NaHSO$_4$.H$_2$O) was added instead of the sulfuric acid to give 3.96 g. (31.9 m. moles) of 3-methylcatechol and 1.67 g. (13.5 m.moles) of 2-methylhydroquinone. The yield of dihydric alkylphenols was 65.4%.

EXAMPLE 44

Into a reaction vessel were charged 150 g. (1390.0 m.moles) of m-cresol, 4.38 g. (P=46.3) of 4-methyl-2-pentanone peroxide and 0.40 g. of 98% sulfuric acid and the reaction was carried out in the same manner as in Example 41 to give 1.36 g. (11.0 m.moles) of 3-methylcatechol, 2.32 g. (18.7 m.moles) of 4-methylcatechol and 2.04 g. (6.5 m.moles) of 2-methylhydroquinone. The yield of dihydric alkylphenols was 99.8%.

EXAMPLES 45-51

The reaction was carried out in the same manner as in Example 41 except that p-cresol was employed instead of the o-cresol and the reaction conditions and the sorts of a ketone peroxide and a catalyst were variously varied. The results are shown in Table 7.

Table 7

| Example No. | p-cresol (g) | Charged formulation Ketone peroxide | | Peroxide amount (P) | Catalyst | | Reaction temperature (° C) | Reaction period (min) | Product 4-methylcatechol Amount produced (g) | Yield (%) |
|---|---|---|---|---|---|---|---|---|---|---|
| | | Sort | (g) | | Sort | (g) | | | | |
| 45 | 150 | methyl ethyl ketone | 7.70 | 46.3 | H$_2$SO$_4$(98%) | 0.40 | 60 | 30 | 3.66 | 63.7 |

Table 7-continued

| Example No. | p-cresol (g) | Charged formulation Ketone peroxide Sort | (g) | Peroxide amount (P) | Catalyst Sort | (g) | Reaction temperature (° C) | Reaction period (min) | Product 4-methylcatechol Amount produced (g) | Yield (%) |
|---|---|---|---|---|---|---|---|---|---|---|
| 46 | " | " | 11.5 | 69.2 | " | " | 100 | 5 | 4.82 | 56.2 |
| 47 | " | " | " | " | NaHSO$_4$ . H$_2$O | 1.00 | " | 30 | 4.58 | 53.3 |
| 48 | " | " | " | " | In$_2$(SO$_4$)$_3$ . 9H$_2$O | 1.50 | " | " | 4.94 | 57.3 |
| 49 | " | " | 23.1 | 139.0 | Strongly acidic ion exchange resin Amberlyst 15 | 1.00 | " | " | 9.32 | 54.1 |
| 50 | " | cyclopentanone peroxide | 10.7 | 43.4 | H$_2$SO$_4$(98%) | 0.40 | " | " | 2.70 | 50.1 |
| 51 | " | methyl phenyl ketone peroxide | 19.9 | 46.3 | KHSO$_4$ | 1.00 | " | " | 2.99 | 52.1 |

EXAMPLE 52

Into a reaction vessel were charged 150 g. (1000.0 m.moles) of p-tert-butylphenol, 3.38 g. (P=35.7) of 4-methyl-2-pentanone peroxide and 0.40 g. of 98% sulfuric acid and the reaction was carried out at 120° C. for 30 minutes in the same manner as in Example 41 to give 3.67 g. (2.21 m.moles) of 4-tert-butylcatechol. The yield of a dihydric alkylphenol was 61.9%.

EXAMPLE 53

The reaction was carried out in the same manner as in Example 41 except that 170 g. (1390.0 m.moles) of p-ethylphenol was employed as a starting material instead of the o-cresol to give 4.33 g. (31.4 m.moles) of 4-ethyl-catechol. The yield of a dihydric alkylphenol was 67.8%.

EXAMPLE 54

Into a 3l-volume flask, which was equipped with a reflux condenser, a thermometer, a stirrer and an outlet for liquid were charged 2052 g. (19.00 moles) of p-cresol and 71.95 g. (P=760) of 4-methyl-2-pentanone peroxide and the flask was maintained at 50° C. Then, 7.4 g. of sodium bisulfate (NaHSO$_4$.H$_2$O) was added and the flask was dipped in an oil bath at 106° C. The reaction was carried out for 30 minutes. Thereafter, the catalyst was removed by extraction with water and vacuum distillation gave 59.37 g. (0.479 mole) of 4-methylcatechol. The yield of a dihydric alkylphenol was 63.0%.

The ketone peroxide which is employed in the following examples 55–66 is the same as defined below or produced in the same manner as shown below.

METHOD FOR THE SYNTHESIS OF A KETONE PEROXIDE

9. Methyl ethyl ketone peroxide (manufactured by Nihon Yushi K.K., Permec N)
   a 55% by weight solution of methyl ethyl ketone peroxide dissolved in dimethyl phthalate. Active oxygen amount 17.5%.
10. 4-Methyl-2-pentanone peroxide (synthesized)
    This peroxide in synthesized in the same manner as in the above 2), and the unreacted ketone is distilled off under reduced pressure to give a sample. Active oxygen amount 11.9%.
11. Methylphenyl ketone peroxide (synthesized)
    This peroxide is synthesized in the same manner as in the above 4), and the unreacted ketone is removed by distillation. Active oxygen amount 8.80%.

EXAMPLE 55

In a reaction vessel equipped with a reflux condenser having water-separating vessel, a thermometer, a stirrer and an outlet for liquid were placed 100 g. (819 m.moles) of 3,5-dimethylphenol and 5.76 g. (P=42.8) of 4-methyl-2-pentanone-peroxide and this reaction vessel was immersed in an oil bath of 150° C. and stirred for 2 hours. During this reaction water was continuously caught in the water-separating vessel. The reaction was analyzed with a gas chromatography to give 1.74 g. (12.6 m.moles) of 3,5-dimethylcatechol and 0.80 g. (5.8 m.moles) of 2,6-dimethylhydroquinone. The yield of dihydric alkylphenol based on peroxide basis as defined in Example 39 was 43.0%. The definition on the yield of dihydric alkylphenols is the same herein below.

EXAMPLE 56

In a vessel used in Example 55, 100 g. (819 m.moles) of 3,5-dimethylphenol, 5.68 g. (P=42.11) of 4-methyl-2-pentanone peroxide and 0.01 g. of 98% sulfuric acid were placed and the reaction was carried out at 100° C. for 20 minutes in the same manner as in Example 55 and analyzed. 3.67 g. (26.6 m.moles) of 3,5-dimethylcatechol and 1.52 g. (11.0 m.moles) of 2,6-dimethylhydroquinone were obtained. The yield of dihydric alkylphenols was 89.3%.

EXAMPLE 57

By following the same manner as in Example 56 except that 0.013 g. of sodium hydrogen sulfate monohydrate (NaHSO$_4$.H$_2$O) was used, 3.42 g. (24.8 m.moles) of 3,5-dimethylcatechol and 1.66 g. (12.0 m.moles) of 2,6-dimethylhydroquinone were obtained. The yield of dihydric alkylphenols was 87.4%.

EXAMPLE 58

By following in the same manner as in Example 56 except that 0.11 g. of strong acidic sulfontype ion exchange resin Amberlyst 15 (manufactured by Rohm and Hass Co.) was used instead of sulfuric acid, 2.55 g. (18.5 m.moles) of 3,5-dimethylcatechol and 1.26 g. (9.1 m.moles) of 2,6-dimethylhydroquinone were obtained. The yield of dihydric alkylphenols was 65.6%.

EXAMPLE 59

By following in the same manner as in Example 56 except that 0.001 g. of 98% sulfuric acid was used and the reaction time was 30 minutes, 3.49 g. (25.9 m.moles) of 3,5-dimethylcatechol and 1.41 (10.2 m.moles) of 2,6-dimethylhydroquinone were obtained. The yield of dihydric alkylphenols was 84.3%.

EXAMPLE 60

By following in the same manner as in Example 56 except that the reaction was carried out at 60° C., 3.24 g. (23.5 m.moles) of 3,5-dimethylcatechol and 1.55 g. (11.2 m.moles) of 2,6-dimethylhydroquinone were obtained. The yield of dihydric alkylphenols was 82.4%.

EXAMPLE 61

By following in the same manner as in Example 56 except that 11.0 g. (P=81.6) of 4-methyl-2-pentanone peroxide was used, 5.80 g. (42.0 m.moles) of 3,5-dimethylcatechol and 2.55 g. (18.5 m.moles) of 2,6-dimethylhydroquinone were obtained. The yield of dihydric alkylphenols was 74.1%.

EXAMPLE 62

By following in the same manner as in Example 56 except that 11.2 g. (P=67.7) of methyl ethyl ketone peroxide was used instead of 4-methyl-2-pentanone peroxide, 4.68 g. (33.9 m.moles) of 3,5-dimethylcatechol and 2.17 g. (15.7 m.moles) of 2,6-dimethylhydroquinone were obtained. The yield of dihydric alkylphenols was 73.3%.

EXAMPLE 63

By following in the same manner as in Example 56 except that 8.77 g. (P=48.3) of methylphenylketone peroxide was used instead of 4-methyl-2-pentanone peroxide, 2.99 g. (21.7 m.moles) of 3,5-dimethylcatechol and 1.48 g. (10.7 m.moles) of 2,6-dimethylhydroquinone were obtained. The yield of dihydric alkylphenols was 67.0%.

EXAMPLE 64

By following in the same manner as in Example 56 except that 100 g. (819 m.moles) of 2,4-dimethylphenol was used instead of 3,5-dimethylphenol, 2.25 g. (16.3 m.moles) of 3,5-dimethylcatechol was obtained. The yield of dihydric alkylphenol was 38.6%.

EXAMPLE 65

By following in the same manner as in Example 56 except that 100 g. (819 m.moles) of 2,6-dimethylphenol was used instead of 3,5-dimethylphenol, 1.04 g. (7.5 m.moles) of 2,6-dimethylhydroquinone was obtained. The yield of dihydric alkylphenol was 17.7%.

EXAMPLE 66

By following in the same manner as in Example 56 except that 100 g. (735 m.moles) of 2,3,5-trimethylphenol was used instead of 3,5-dimethylphenol, 2.16 g. (14.2 m.moles) of 3,4,6-trimethylcatechol and 0.71 g. (4.7 m.moles) of 2,3,5-trimethylhydroquinone were obtained. The yield of dihydric alkylphenols was 44.9%.

What is claimed is:

1. A process for preparing a dihydric phenol having the formula:

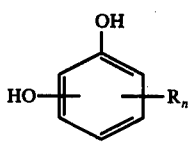

wherein R represents a lower alkyl radical having 1-6 carbon atoms and each R may be the same or different, and $n$ represents zero or an integer of 1 to 4 and when $n$ is 3 or 4 not all of the 3-, 4- and 6-positions are occupied with the said alkyl radicals, which comprises oxidizing a monohydric phenol having the formula

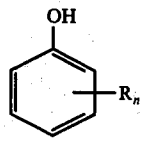

wherein R and $n$ have the same meanings as above, with a ketone peroxide at a temperature of from 45° to 200° C. in the absence of a catalyst, the amount of peroxide P per millimole of the monohydric phenol being a value of from 0.01 to 0.50, said ketone peroxide being obtained by reaction of hydrogen peroxide and a ketone selected from the group consisting of (i) and (ii), following:

i. a ketone having 3–20 carbon atoms represented by the following formula:

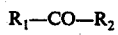

wherein $R_1$ and $R_2$, which may be the same or different, and which represent straight or branched alkyl groups of 1–8 carbon atoms or a phenyl group, or ii. a cycloketone having the following formula:

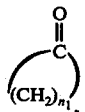

wherein $n_1$ represents an integer of 4–11, inclusive, or a ketone peroxide derived from a secondary alcohol having the following formula:

iii. a secondary alcohol having 3–20 carbon atoms and represented by the following formula:

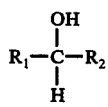

wherein R and R have the same meanings as above.

2. The process as claimed in claim 1 wherein phenol is used as starting material.

3. The process as claimed in claim 1 wherein a monohydric monoalkyl phenol having an alkyl radical with 1-6 carbon atoms is used as starting material.

4. The process as claimed in claim 1 wherein a monohydric polyalkylphenol having the formula:

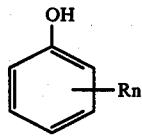

wherein $n$ represents an integer of 2–4 and R$s$ have the same meanings as in claim 1 and when $n$ is 3 or 4, there is no case where all of 2-, 4-, and 6-positions are occupied with the alkyl radicals is used to obtain a dihydric polyalkylphenol having the formula:

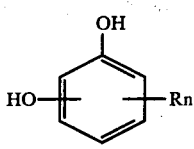

wherein R and n have the same meanings as above.

5. The process as claimed in claim 1 wherein the reaction is carried out at a temperature of 45° to 200° C.

6. The process as claimed in claim 1 wherein a ketone peroxide selected from 4-methyl-2-pentanone peroxide, methyl phenyl ketone peroxide, methyl ethyl ketone peroxide and cyclopentanone peroxide is used.

7. A process for preparing a dihydric phenol having the formula:

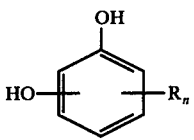

wherein R represents a lower alkyl radical having 1–6 carbon atoms and each R may be the same or different, and n represents zero or an integer of 1 to 4 and when n is 3 or 4 not all of the 2-, 4- and 6-positions are occupied with the said alkyl radicals, which comprises oxidizing a monohydric phenol having the formula:

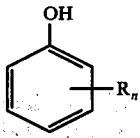

wherein R and n have the same meanings as above, with a ketone peroxide at a temperature of from 45° to 200° C. in the presence of a catalyst selected from the group consisting of sulfuric acid and a salt thereof and a sulfonic acid and a salt thereof, the amount of peroxide P per millimole of the monohydric phenol being a value of from 0.01 to 0.50, said ketone peroxide being obtained by reaction of hydrogen peroxide and a ketone selected from the group consisting of (i) and (ii), following:

i. a ketone having 3–20 carbon atoms represented by the following formula:

$$R_1-CO-R_2$$

wherein $R_1$ and $R_2$, which may be the same or different, and which represent straight or branched alkyl groups of 1–18 carbon atoms or a phenyl group, or ii. a cycloketone having the following formula:

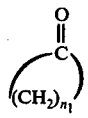

wherein $n_1$ represents an integer of 4–11, inclusive, or a ketone peroxide derived from a secondary alcohol having the following formula:

iii. a secondary alcohol having 3–30 carbon atoms and represented by the following formula:

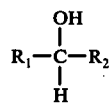

wherein $R_1$ and $R_2$ have the same meanings as above

8. The process as claimed in claim 7 wherein an amount of catalyst used is not less than 0.0001% by weight with respect to the monohydric phenol.

9. The process of claim 7, wherein the cataylst is sulfuric acid.

10. The process of claim 7, wherein the catalyst is zinc sulfate.

11. The process of claim 7, wherein the catalyst is p-toluene sulfonic acid.

* * * * *

UNITED STATES PATENT AND TRADEMARK OFFICE
CERTIFICATE OF CORRECTION

PATENT NO. : 4,072,722
DATED : February 7, 1978
INVENTOR(S) : SUMIO UMEMURA et al It is certified that error appears in the above-identified patent and that said Letters Patent are hereby corrected as shown below:

Column 1, line 24: "which...derivatives (II):" should be printed on a separate line; lines 34-35: "with a ketone peroxide" should be printed on a separate line.

Column 1, line 40: "Partische" should be ---Praktische---.

Column 2, lines 26-27: "monyhydric" should be ---monohydric---.

Column 5, line 38: "7nonadecen-2-ol" should be ---7-nonadecen-2-ol---.

Column 6, line 15: replace "-0.0-" with --- $-O \cdot O-$ ---.

Column 6, lines 20-21: replace "O!$I_2$" with --- $O \to I_2$ ---.

Column 10, line 40: replace "p" with ---P---.

Column 10, Table 4, first column: below "12", replace "3" with ---13---.

Column 11, Table 5, second column: insert a slash (/) between "Methyl ethyl..." and "Phenol...".

Column 12, line 29: replace "1,03" with ---1.03---.

Column 12, line 66: replace "2.17" with ---2.17 g.---.

UNITED STATES PATENT AND TRADEMARK OFFICE
CERTIFICATE OF CORRECTION

PATENT NO. : 4,072,722
DATED : February 7, 1978
INVENTOR(S) : SUMIO UMEMURA et al It is certified that error appears in the above-identified patent and that said Letters Patent are hereby corrected as shown below:

Column 12, line 56: replace "kg./$cm^2$and" with ---kg./$cm^2$ and---.

Column 12, line 60: before "iodometry", delete "a".

Column 13, line 3: after "0.153g.", delete "of".

Column 13, line 10: "0.0150" should be ---0.150---.

Columns 13-14, Table 7, third column: after "methyl ethyl ketone", insert ---peroxide---.

Column 15, line 61: before "synthesized", replace "in" with ---is---.

Column 15, line 66: replace "snythesized" with ---synthesized---.

Column 16, line 66: replace "1.41" with ---1.41 g.---.

Column 18, line 1: replace "?-, 4- and 6-" with ---2-, 4- and 6- ---.

Column 18, line 28: replace "1-8" with ---1-18---.

Column 18, line 49: replace "R  and R " with ---$R_1$ and $R_2$---.

UNITED STATES PATENT AND TRADEMARK OFFICE
CERTIFICATE OF CORRECTION

PATENT NO. : 4,072,722                      Page 3 of 3

DATED : February 7, 1978

INVENTOR(S) : SUMIO UMEMURA et al

It is certified that error appears in the above-identified patent and that said Letters Patent are hereby corrected as shown below:

Column 18, line 65: replace "Rs have" with ---R has---.

Column 20, line 25: replace "3-30" with ---3-20---.

Signed and Sealed this

Thirtieth Day of September 1980

[SEAL]

Attest:

SIDNEY A. DIAMOND

Attesting Officer        Commissioner of Patents and Trademarks